United States Patent
Waditschatka et al.

(10) Patent No.: US 6,664,422 B1
(45) Date of Patent: Dec. 16, 2003

(54) PROCESS FOR THE PREPARATION OF STROBILURIN INTERMEDIATES

(75) Inventors: Rudolf Waditschatka, Gipf-Oberfrick (CH); René Zurflüh, Bülach (CH); Edward Kelsall, Hessle (GB); Hugo Ziegler, Witterswil (CH); Linhua Wang, Baton Rouge, LA (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/857,391

(22) PCT Filed: Dec. 9, 1999

(86) PCT No.: PCT/EP99/09705
§ 371 (c)(1),
(2), (4) Date: Aug. 13, 2001

(87) PCT Pub. No.: WO00/34229
PCT Pub. Date: Jun. 15, 2000

(30) Foreign Application Priority Data

Dec. 10, 1998 (GB) .............................................. 9827163

(51) Int. Cl.$^7$ ..................... C07C 249/00; C07C 251/00; C07C 259/00; C07C 291/00
(52) U.S. Cl. ..................... 564/253; 564/248; 564/256; 564/259; 564/265
(58) Field of Search ............................. 564/248, 253, 564/256, 259, 265

(56) References Cited

U.S. PATENT DOCUMENTS

| | | | |
|---|---|---|---|
| 5,889,059 A | 3/1999 | Bayer et al. | 514/619 |
| 5,981,581 A | 11/1999 | Bayer et al. | 514/522 |
| 6,100,263 A | 8/2000 | Bayer et al. | 514/241 |
| 6,187,812 B1 | 2/2001 | Bayer et al. | 514/522 |

FOREIGN PATENT DOCUMENTS

| | | |
|---|---|---|
| DE | 19 719 054 | 11/1998 |
| WO | 95/18789 | 7/1995 |
| WO | 95/21153 | 8/1995 |
| WO | 96/11183 | 4/1996 |
| WO | 97/20808 | 6/1997 |

OTHER PUBLICATIONS

Organic Syntheses Coll., vol. 3, pp. 172–174, (date unavailable) submitted by H.S. Anker & H.T. Clarke, Carboxymethoxylamine Hemihydrochloride.

*Primary Examiner*—Johann Richter
*Assistant Examiner*—Elvis O. Price
(74) *Attorney, Agent, or Firm*—Richard E.L. Henderson

(57) ABSTRACT

The present invention relates to a novel improved process and intermediates for the process of preparing the oxime intermediates of formula (II) wherein $R_1$ is hydrogen, fluoro or chloro, and $R_2$ is methyl, ethyl, methoxy, ethoxy, trifluoromethyl, trifluoromethoxy, cyano, fluoro, chloro or bromo. The novel process comprises diazotizing an aniline of formula (VI) reacting the resulting diazonium salt with isopropenylacetate of formula (X) and reacting the resulting ketone of formula (XI) with an organic nitrite in the presence of hydrogene chloride, and methylating the resulting ketooxime of formula (VIII) with a methylating agent and reacting the resulting O-methyl ketooxime of formula (IX) with hydroxylamine. The compounds of formula (II) are intermediates for highly active fungicides from the class of the strobilurins.

2 Claims, No Drawings

PROCESS FOR THE PREPARATION OF STROBILURIN INTERMEDIATES

This application is a 371 of PCT/EP49/04705, filed Dec. 4, 1999.

FIELD OF THE INVENTION

The present invention relates to a novel improved process of preparing certain intermediates for highly active fungicides from the class of the strobilurins. Another aspect of the invention are the novel intermediates per se which have been prepared for the process of this invention.

SUMMARY OF THE INVENTION

The fungicidal strobilurins have previously been described in e.g. WO-A-95/18789 or the later WO-A-95/21153 and WO-A-95/21154. The processes disclosed therein are typical laboratory routes which for large scale production are not in all steps suitable. The present invention now provides a new improved process designed for large scale industrial production which allows the production of strobilurins and its key intermediates in an industrial production process.

DETAILED DESCRIPTION

The fungicidal strobilurins have the general formula I

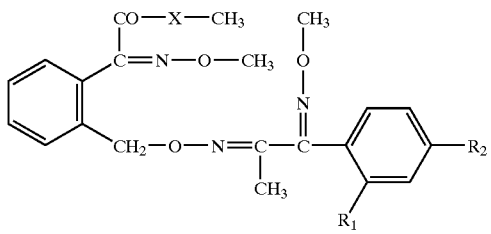

(I)

wherein $R_1$ is hydrogen, fluoro or chloro, $R_2$ is methyl, ethyl, methoxy, ethoxy, trifluoromethyl, trifluoromethoxy, cyano, fluoro, chloro or bromo, and X is NH or oxygen.

The known individual strobilurins of formula I are listed in the following table

TABLE 1

| Comp. No. | $R_1$ | $R_2$ | X |
|---|---|---|---|
| 01 | H | Cl | O |
| 02 | H | Cl | NH |
| 03 | H | F | O |
| 04 | H | F | NH |
| 05 | F | H | O |
| 06 | F | H | NH |
| 07 | Cl | H | O |
| 08 | Cl | H | NH |
| 09 | Cl | Cl | O |
| 10 | Cl | Cl | NH |
| 11 | F | F | O |
| 12 | F | F | NH |
| 13 | Cl | F | O |
| 14 | Cl | F | NH |
| 15 | F | Cl | O |
| 16 | F | Cl | NH |
| 17 | H | Br | O |
| 18 | H | Br | NH |
| 19 | H | CN | O |
| 20 | H | CN | NH |
| 21 | H | $CH_3$ | O |
| 22 | H | $CH_3$ | NH |
| 23 | H | $OCH_3$ | O |
| 24 | H | $OCH_3$ | NH |
| 25 | H | $C_2H_5$ | O |
| 26 | H | $C_2H_5$ | NH |
| 27 | H | $CF_3$ | O |
| 28 | H | $CF_3$ | NH |
| 29 | H | $OC_2H_5$ | O |
| 30 | H | $OC_2H_5$ | NH |

The fungicidal strobilurins of formula I are synthesized by a conventional etherification step from the oxime compound of formula II

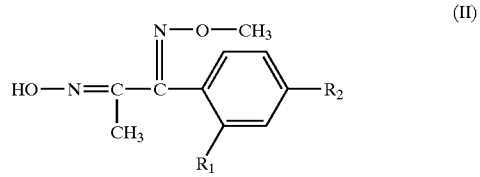

(II)

wherein $R_1$ and $R_2$ are as defined for formula I in the presence of a base with the coupling component III

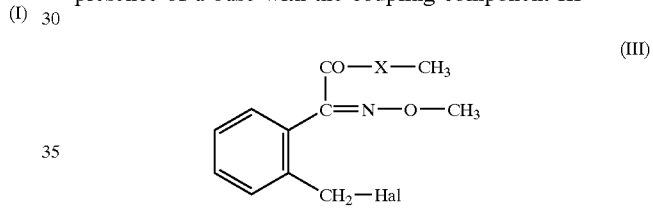

(III)

wherein X is as defined for formula I and Hal is halogen, preferably chlorine or bromine.

The coupling components III and most of the members of the oximes of formula II are known.

According to the process of this invention the oximes of formula II are obtained by the process comprising reacting a propiophenone of formula IV

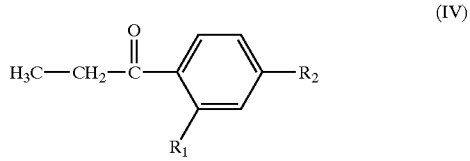

(IV)

wherein $R_1$ and $R_2$ are as defined for the compounds of formula I in the presence of hydrogen chloride with an organic nitrite, e.g. alkyl nitrite such as iso- or n-pentyl nitrite, and converting the resulting ketooxime of formula V

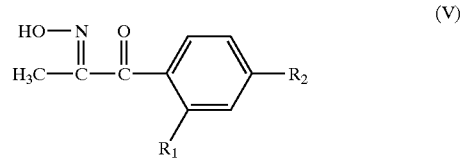

(V)

wherein $R_1$ and $R_2$ are as defined for the compounds of formula I into the compound of formula II by reacting it with an aqueous solution of O-methyl-hydroxylamine-hydrochloride, and subsequent isomerisation of the (E,E/E,Z)-mixture of compound II into predominantly the (E/E)-form thereof.

The two-step process of the invention (IV→V→II) may be carried out in large industrial scale vessels. The first step (IV→V) is advantageously conducted in an inert organic solvent, e.g. tetrahydrofurane, dioxane, toluene, xylenes or a cyclic hydrocarbon like cyclohexane, methylcyclohexane, or iso or n-pentanol, etc. at temperatures between −20° C. and +60° C., with −5° C. to +40° C., and especially +25° C. to +40° C., and even more +10° C. to +40° C. being preferred. In the second step the keto group is replaced by the methoximino function in a single step reaction. The resulting intermediate may be isomerised in situ in the work-up solution and it may be isolated therefrom, if desired. However, for the large scale production process it is even more advantageous to use the work-up solution directly for the coupling of intermediate II with the intermediate III.

The product of formula II is preferably used in the from of the (E,E)-isomer for further coupling with the compound of formula III for producing the fungicidal stobilurins.

Alternatively, the compounds of formula II may be obtained by diazotizing an aniline of formula VI

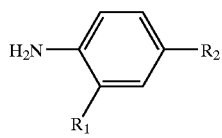

(VI)

and reacting the resulting diazonium salt with methylglyoxal-1-oxime of formula VII

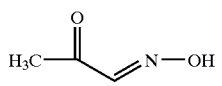

(VII)

and methylating the resulting ketooxime of formula VIII

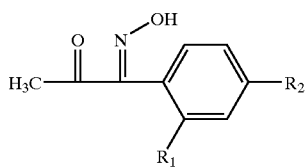

(VIII)

with an methylating agent and reacting the resulting O-methyl ketooxime of formula IX

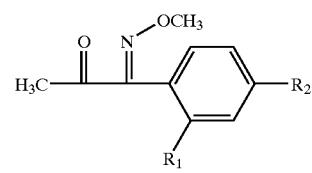

(IX)

with hydroxylamine.

Alternatively, in a variant the compounds of formula VII may be obtained by diazotizing an aniline of the formula VI and reacting the resulting diazonium salt with isopropenylacetate of formula X

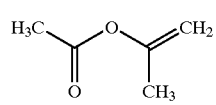

(X)

and reacting the resulting ketone of formula XI

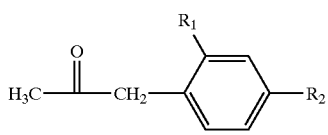

(XI)

with an organic nitrite in the presence of hydrogene chloride.

The diazotization reaction is carried out in an organic solvent with an organic nitrite, e.g. an alkyl nitrite as isoamyl nitrite, or an aryl nitrite, as phenyl nitrte; or, more preferably, in aqueous solution with nitrous acid or a salt thereof, in presence of an acid. Preferred nitrites are sodium nitrite, potassium nitrite, magnesium nitrite, particularly preferred is sodium nitrite. Preferred acids are hydrochloric acid, sulfuric acid and nitrosulfuric acid.

Advantageous is a temperature of −10° C. to +30° C. and a pH 0–3.

The diazonium compound is preferably reacted in the presence of $CuCl_2$ or $CuSO_4$ at −10° C. to +40° C., more preferably −10° C. to +15° C., and at pH 2–7, more preferably at pH 3–5. The amount of the copper salt is 1 to 20 mol %, more preferably 3 to 6 mol %, in relation to the aniline of formula VI.

Methylation of the ketooxime of formula VII is carried out with a methylating agent such as methyl iodide, dimethylsulfate or diazomethane in presence of a base, e.g. potassium carbonate or sodium hydride in a suitable solvent at suitable reaction temperatures as described by H. S. Anker and H. T. Clarke in Organic Synthesis, Coll. Vol. 3,172.

The introduction of the oxime function into the intermediate of formula XI is preferably carried out in an inert organic solvent, e.g. tetrahydrofurane, dioxane, toluene, xylenes or a cyclic hydrocarbon like cyclohexane, methylcyclohexane, or iso- or n-pentanol, etc. at temperatures between −20° C. and +60° C., with −5° C. to +40° C., and especially +25° C. to 40° C. and even more +10° C. to +40° C. in the presence of e.g. hydrogen chloride by treatment with an organic nitrite, e.g. an alkyl nitrite as iso- or n-pentyl nitrite, or an aryl nitrite, as phenyl nitrite According to the process of the invention the following intermediates of formula II may be obtained with high yields. Novel intermediates of formula II constitute another feature of the present invention.

TABLE 2

| Intermediates of formula II | | |
|---|---|---|
| Comp. No. | $R_1$ | $R_2$ |
| 01 | H | Cl |
| 02 | H | F |
| 03 | F | H |
| 04 | Cl | H |
| 05 | Cl | Cl |
| 06 | F | F |
| 07 | Cl | F |
| 08 | F | Cl |
| 09 | H | Br |

TABLE 2-continued

Intermediates of formula II

| Comp. No. | $R_1$ | $R_2$ |
|---|---|---|
| 10 | H | CN |
| 11 | F | $CH_3$ |
| 12 | H | $OCH_3$ |
| 13 | H | $C_2H_5$ |
| 14 | H | $CF_3$ |
| 15 | H | $OC_2H_5$ | following Examples serve as illustration of the invention and in no way present any limitation.

EXAMPLE 1

(E,E/E,Z)-1-(4-Chloro-phenyl)-propane-1,2-dione-1-(O-methyl-oxime)-2-oxime

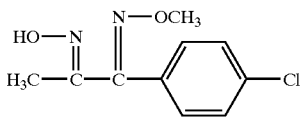

(E)-1-(4-Chlorophenyl)-propan-1,2-dione-2-oxime

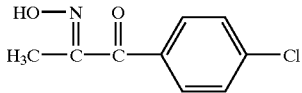

To a solution of 440 g (2.437 mol) of 4-chloropropiophenone and 335 g (2.925 mol) t-butylnitrite in 700 g of tetrahydrofurane 97.8 g (2.681 mol) of gaseous hydrochloric acid is dosed over 2 hours at +25° C. to +40° C. Following the end of the addition the batch is stirred for two hours at +15° C. to +30° C. The reaction mixture is neutralized by adding 630.5 g of 20% sodium carbonate solution at +25° C. Some brine and methylcyclohexane is added and the phases are separated. The product crystallizes from the organic phase when concentrated. The product is isolated by filtration and the filter cake is washed with 75 g of methylcyclohexane at 0° C.: 438.9 g of (E)-1-(4-chlorophenyl)-propan-1,2-dione-2-oxime (m.p. 115–115C.) are obtained in 91.1% yield.

b) To 200 g of chlorobenzene are added 99.8 g (0.50 mol) of (E)-1-(4-chlorophenyl)-propan-1,2-dione-2-oxime and 192.7 g (0.60 mol) of a 26% aqueous solution of O-methylhydroxyl-amine-hydrochloride. The pH of the resulting solution is adjusted to 3.3 by the addition of 100 g (1.26 mol) pyridine. Following the dosing the reaction mixture is stirred for 7 hours at the reaction temperature of +75° C. The reaction mixture is concentrated by evaporation of chlorobenzene and the residue is stirred with water and ethyl acetate. The organic phase is washed neutral with HCl 32% and water and the combined aqueous phases are again extracted with ethyl acetate. On evaporation of the solvent the product is crystallized from methylcyclohexane and dried. Yield: 95.7 g (E,E/E,Z)-1-(4-chloro-phenyl)-propane-1,2-dione-1-(O-methyl-oxime)-2-oxime (yield 84.0% of the 1:1 isomer mixture), m.p. 162° C.

EXAMPLE 2

(E,E/E,Z)-1-(2,4-Difluoro-phenyl)-propane-1,2-dione 1-(O-methyl-oxime)-2-oxime

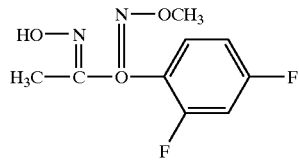

a) 1-(2,4-Difluoro-phenyl)-propane-1,2-dione 1-oxime

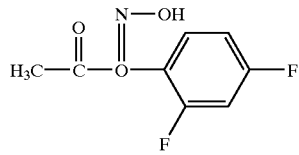

With stirring 10.0 g (0.1 mol) of sulfuric acid (95–97%) are diluted with 45 ml of water. At +20° C. 12.9 g (0.1 mol) of 2,4-difluoroaniline are added in one portion. The solution warms up to +38° C. and the 2,4-difluoroaniline-sulfate precipitates as a white crystalline powder. The suspension is cooled to 0° C. Within 20 minutes continuously a solution of 7.0 g (0.101 mol) sodium nitrite in 30 ml of water is added at 0° C. to 5° C. Close to the end of the addition the diazonium salt suspension is diluted with 150 ml of water to allow further stirring. The viscous suspension is allowed to be stirred for another 15 minutes before 0.6 g of amidosulfuric acid in 4 ml of water are added to inactivate the excess nitrite.

In a separate beaker to a mixture of 8.3 g sulfuric acid (95–97%) and 60 ml of water 8.7 g of anti-methylglyoxal-1-oxime is added. To this mixture 5.0 g of copper sulfate pentahydrate and 5 g of sodium sulfite are added. The dark-greenish solution is cooled to 0° C. and stored.

With vigorous stirring and cooling the diazonium salt solution is added within 10 minutes to the anti-methylglyoxal-oxime solution at 0° C. The viscous suspension is stirred for 5 hours at 0° C. and then with continued stirring for 16 hours allowed to warm up to room temperature. After this period the yellow suspension can be stirred easily.

The mixture is saturated with solid NaCl and filtered. The brownish residue is washed with 50 ml of water. This crude product is taken up with 100 ml of 1N sodium hydroxide solution and again filtered. The residue is discarded. The orange filtrate is added to 40 g of ice and adjusted to pH 1 by adding 2N HCl. The solid residue is separated and washed with water. For further purification the residue is solved in 300 ml of ethyl acetate/hexane (1:1) and filtered through 20 g of silicagel. Evaporating of the solvent and drying yields 7.52 g of 1-(2,4-difluoro-phenyl)-propane-1,2-dione-1-oxime, m.p. 126–129° C. After recrystallisation from methylcyclohexanone the melting point is 133–135° C.

b) (E)-1-(2,4-Difluoro-phenyl)-propane-1,2-dione-1-(O-methyl-oxime)

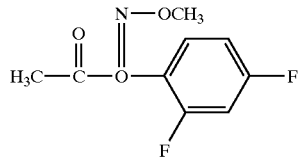

258 g potassium carbonate is added to a solution of 310 g 1-(2,4-difluoro-phenyl)-propane-1,2-dione-1-oxime in 2 l acetonitrile. After stirring for a half hour 265 g methyl iodide is added dropwise at +35° C. to +40° C. The reaction mixture is stirred for 5 hours and then diluted with 2 l water. After extraction with 5 l ethyl acetate the organic layer is washed two fold with 2 l sodium chloride solution (25%) and dried with sodium sulfate. After evaporation of the volatile parts 323 g of a brown oil remain, which is purified by heating at +70° C. in 1.2 l toluene containing 100 g Hyflo and 13 g activated carbon for 10 minutes followed by filtration of the cold solution through silicagel. Evaporating of the solvent and drying yields 317 g of an orange oil containing 80% of (E)-1-(2,4-difluoro-phenyl)-propane-1,2-dione-1-(O-methyl-oxime).

c) (E,E)-1-(2,4-Difluoro-phenyl)-propane-1,2-dione-1-(O-methyl-oxime)-2-oxime

A solution of 4.26 g (E)-1-(2,4-difluoro-phenyl)-propane-1,2-dione-1-(O-methyl-oxime) and 1.5 g hydroxylamine hydrochloride in 20 ml pyridine is heated to +90° C. for 2 hours. After addition of 50 ml ice-cold water a yellow oil precipitates, which crystallizes within several hours. Filtration, washing with water and drying yields 4.4 g of a yellow solid. Purification by recrystallization in ethyl acetate/hexane gives 4.0 g (E,E)-1-(2,4-difluoro-phenyl)-propane-1,2-dione-1-(O-methyl-oxime) 2-oxime as white crystals, m.p 115–117° C.

EXAMPLE 3

(E,E/E,Z)-1-(2,4-Difluoro-phenyl)-propane-1,2-dione-1-(O-methyl-oxime)-2-oxime

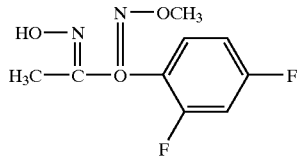

a) (E)-1-(2,4-Difluoro-phenyl)-propane-1,2-dione-2-oxime

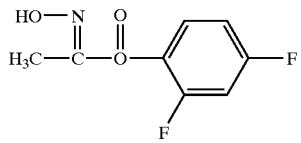

To a solution of 170 g (1.00 mol) of 2,4-difluoropropiophenone in 200 g methylcyclohexane 37 g (1.01 mol) of gaseous hydrochloric acid is dosed over 3 hours at 0° C. Thereafter 120 g (1.04 mol) of pentylnitrite are added over a period 3 to 4 hours to the reaction mixture at +10° C. to +15° C. Following the end of the addition the batch is stirred for an hour at +10° C. to +15° C. during which time a suspension is formed. The reaction mixture is then cooled to 0° C. and stirred for a further hour. The product is isolated by filtration and the filter cake is washed with 75 g of methylcyclohexane at 0° C.: 176 g of (E)-1-(2,4-difluoro-phenyl)-propane-1,2-dione-2-oxime (m.p. 99–101° C.) are obtained in 88.6% yield.

b) To 400 g of toluene are added 200 g (1.00 mol) of (E)-1-(2,4-difluoro-phenyl)-propane-1,2-dione-2-oxime and 338 g (1.21 mol) of a 30% aqueous solution of O-methylhydroxyl-amine-hydrochloride. The resulting mixture is heated to +65° C. and 178 g (1.76 mol) of triethylamine is dosed over 1.5 to 2 hours. During the dosing the internal temperature is allowed to rise to +85° C. Following the dosing the reaction mixture is stirred for a further 10 hours at the reaction temperature of +85° C. The pH of the reaction mixture is then adjusted at +30° C. to +35° C. to less than pH 0.7 by the addition of approximately 30 g (0.26 mol) of 32% hydrochloric acid. Subsequent phase separation removes with the aqueous stream the waste containing triethylamine-hydrochloride. The (E,E/E,Z)-1-(2,4-difluoro-phenyl)-propane-1,2-dione-1-(O-methyl-oxime)-2-oxime product is separated from its side products by the addition of 200 g of water and 171 g (1.29 mol) of a 30% sodium hydroxide solution at +20° C. to +25° C. A second extraction with 50 g of water and 41 g (0.31 mol) of a 30% sodium hydroxide solution is performed. The toluene stream containing the by-product waste is removed by phase separation. The (E,E/E,Z)-1-(2,4-difluoro-phenyl)-propane-1,2-dione-1-(O-methyl-oxime)-2-oxime product is set free from its sodium salt form by the addition of approximately 200 g (1.75 mol) of 32% hydrochloric acid at +20° C. to +25° C. and 338 g of fresh toluene is added in order to extract the organic product. The pH of the mixture is adjusted to less than pH 0.7 by the addition of a further small quantity of 32% hydrochloric acid. Phase separation removes the aqueous phase containing the salt waste. Isomerisation of the product to a isomer ratio (E,E/E,Z: 92:8) is obtained (if desired) by the addition of 7 g (0.06 mol) of 32% hydrochloric acid at +63° C. to +65° C. followed by a 2 hour period of stirring. The addition of 78 g of water at +63° C. to +65° C. and a subsequent phase separation removes final traces of acid. Any remaining traces of water are removed with an azeotropic vacuum distillation. Finally 82 g of 1-methyl-2-pyrrolidone are added to the product solution to prevent product precipitation during storage at room temperature. The yield of the reaction (all isomers) is 64%, giving a 100% content of 146 g (0.64 mol) for the product solution.

EXAMPLE 4

{2-[2-(4-Chloro-phenyl)-2-methoxyimino-1-methyl-ethylidene-aminooxymethyl]-phenyl}-methoxyimino-acetic acid methyl ester

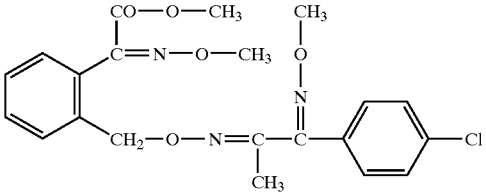

To 150 ml of acetonitrile are added 17.0 g (75.0 mmol) 1-(4-chloro-phenyl)-propane-1,2-dione 1-(O-methyl-oxime) 2-oxime, 21.5 g (75.0 mmol) of (2-bromomethyl-phenyl)-methoxyimino-acetic acid methyl ester and 16.6 g (120 mmol) of potassium carbonate. The resulting suspension is heated at +80° C. for 3 hours. At room temperature 400 ml of water is added to the suspension followed by an extraction with 3×200 ml ethyl acetate. The organic product phase is washed with 2×200 ml water and then dried over magnesium sulfate and filtered. To the crude product oil obtained by solvent evaporation hexane is added whereafter the pure {2-[2-(4-chloro-phenyl)-2-methoxyimino-1-methyl-ethylideneaminooxymethyl]-phenyl}-methoxyimino-acetic acid methyl ester crystallizes from hexane: 25.5 g, 78.7% of theory, m.p. 115–117° C.

EXAMPLE 5

{2-[2-(2,4-Difluoro-phenyl)-2-methoxyimino-1-methyl-ethylidene-aminooxymethyl]-phenyl}-methoxyimino-acetic acid methyl ester

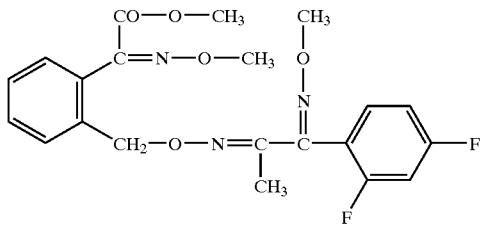

To 150 ml of acetonitrile are added 17.1 g (75.0 mmol) The (E,E/E,Z)-1-(2,4-difluoro-phenyl)-propane-1,2-dione- 1-(O-methyl-oxime) 2-oxime, 21.5 g (75.0 mmol) of (2-bromomethyl-phenyl)-methoxyimino-acetic acid methyl ester and 16.6 g (120 mmol) of potassium carbonate. The resulting suspension is heated at +80° C. for 3 hours. At room temperature 400 ml of water is added to the suspension followed by an extraction with 3×200 ml ethyl acetate. The organic product phase is washed with 2×200 ml water and then dried over magnesium sulfate and filtered. To the crude product oil obtained by solvent evaporation hexane is added whereafter the pure {2-[2-(2,4-difluoro-phenyl)-2-methoxyimino-1-methyl-ethylideneaminooxymethyl]-phenyl}-methoxyimino-acetic acid methyl ester crystallizes from hexane: 24.9 g, 76.6% of theory. The product is a mixture of two isomers, E,E,E and E,E,Z, at a ratio of 87:13, m.p. 110–119° C.

EXAMPLE 6

1-(2,4-Difluoro-phenyl)-propane-2-one

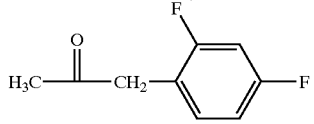

With stirring and cooling 132.0 g (1.32 mol) of concentrated sulfuric acid are diluted with 375 ml of water. At 10–15° C. 78.7 g (0.60 mol) of 2,4-difluoroaniline are added and the resulting suspension is treated with 104.6 g (0.606 mol) of a 40% solution of sodium nitrite in water at 0–3° C. over 45 minutes.

In a separate reactor a mixture is prepared from 6.0 g copper sulfate pentahydrate, 180 ml of water, 0.9 g of concentrated sulfuric acid and 91.2 g (0.90 mol) of isopropenyl acetate. To this mixture the diazonium salt solution and 50.4 g of an aqueous 20% sodium sulfite solution is concurrently added over a period of 2 hours at 10–15° C. The mixture is stirred for another hour before it is extracted with two portions of toluene. The combined organic layers are washed with a diluted bicarbonate solution and brine. The solvent is removed under reduced pressure and the residual crude oil is distilled at 75–80° C./5 mbar: 85.8 g of pale yellow 1-(2,4-difluoro-phenyl)-propane-2-one are obtained in 82.9% yield.

EXAMPLE 7

(E)-1-(2,4-Difluoro-phenyl)-propane-1,2-dione 1-oxime

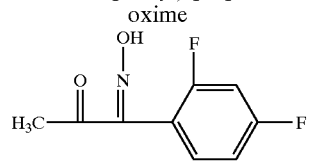

A solution of 140.2 g (0.80 mol) of 1-(2,4-difluoro-phenyl)-propane-2-one in 550 g of methylcyclohexane is warmed up to 30–35° C. Over a period of 2 hours 96.6 g (0.80 mol) of isoamyl nitrite is added while a slow stream of dry hydrogen chloride is fed subsurface into the reactor. Following the end of the addition the batch is stirred for 15 minutes at 30–35° C. before the suspension is cooled to 0° C. The product is isolated by filtration and the filter cake is washed with 150 g of methylcyclohexane at 0° C.: 146.9 g of (E)-1-(2,4-difluoro-phenyl)-propane-1,2-dione 1-oxime (mp. 133–135° C.) are obtained in 89.5% yield.

What is claimed is:
1. A process for preparing an oxime of formula II

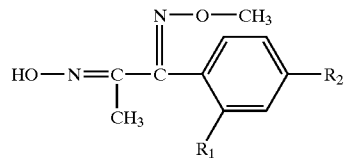

(II)

wherein $R_1$ is hydrogen, fluoro or chloro, and $R_2$ is methyl, ethyl, methoxy, ethoxy, trifluoromethyl, trifluoromethoxy, cyano, fluoro, chloro or bromo, comprising the steps of diazotizing an aniline of formula VI

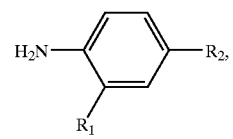

(VI)

reacting the resulting diazonium salt with isopropenylacetate of formula X

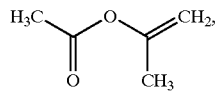

(X)

reacting the resulting ketone of formula XI

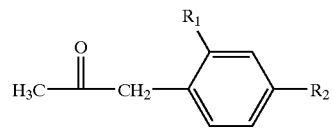

(XI)

with an organic nitrite in the presence of hydrogen chloride, methylating the resulting ketooxime of formula VIII

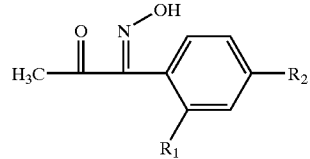

(VIII)

with a methylating agent, and reacting the resulting O-methyl ketooxime of formula IX

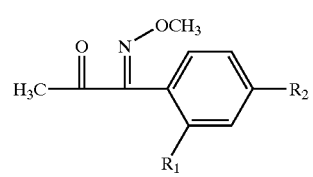

(IX)

with hydroxylamine.

2. A process according to claim 1, wherein when $R_1$ is H then $R_2$ is Cl, F, Br, CN, $CH_3$, $OCH_3$, $C_2H_5$, $CF_3$, $OC_2H_5$; and when $R_1$ is F or Cl then $R_2$ is H, Cl, F.

* * * * *